United States Patent
Tun et al.

(10) Patent No.: US 8,790,300 B2
(45) Date of Patent: Jul. 29, 2014

(54) DUAL BALLOON CATHETER

(75) Inventors: Zaya Tun, Livermore, CA (US); Raj Subramaniam, Fremont, CA (US); Judy Del Rosario, San Jose, CA (US); Lorna Fosse, San Jose, CA (US); Desmond Cheung, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 243 days.

(21) Appl. No.: 13/312,681

(22) Filed: Dec. 6, 2011

(65) Prior Publication Data

US 2012/0143131 A1 Jun. 7, 2012

Related U.S. Application Data

(60) Provisional application No. 61/420,209, filed on Dec. 6, 2010.

(51) Int. Cl.
*A61M 29/00* (2006.01)
(52) U.S. Cl.
USPC .................................................. 604/101.02
(58) Field of Classification Search
USPC ............... 604/101.01, 101.02, 101.03, 99.01, 604/103.01, 509, 915; 606/192, 194, 193, 606/108; 600/3, 7
See application file for complete search history.

(56) References Cited

U.S. PATENT DOCUMENTS

| | | | |
|---|---|---|---|
| 6,638,245 B2 | 10/2003 | Miller et al. | |
| 7,220,252 B2 * | 5/2007 | Shah | 604/500 |
| 2009/0299355 A1 | 12/2009 | Bencini et al. | |
| 2010/0076402 A1 | 3/2010 | Mazzone et al. | |
| 2010/0100087 A1 | 4/2010 | Mazzone et al. | |

* cited by examiner

*Primary Examiner* — Nicholas Lucchesi
*Assistant Examiner* — Brooke Matney
(74) *Attorney, Agent, or Firm* — Seager, Tufte & Wickhem, LLC

(57) ABSTRACT

Methods and devices for bonding a balloon assembly, such as a balloon assembly including an inner balloon and an outer balloon, to a catheter shaft are disclosed. In some cases, a proximal waist of the inner balloon may be bonded to an interior surface of an outer tubular member of the catheter shaft and a proximal waist of the outer balloon may be bonded to an exterior surface of the outer tubular member. In other cases, the proximal waist of the inner balloon may be bonded to a reduced diameter portion of the outer tubular member of the catheter shaft and the proximal waist of the outer balloon may be bonded to the outer tubular member, such as a non-reduced outer diameter portion of the outer tubular member.

19 Claims, 5 Drawing Sheets

DUAL BALLOON CATHETER

CROSS-REFERENCE TO RELATED APPLICATION

This application claims the benefit of U.S. Provisional Application Ser. No. 61/420,209, filed Dec. 6, 2010, the entire disclosure of which is incorporated herein by reference.

FIELD

The present disclosure relates generally to medical devices and, more particularly, to dual balloon catheters.

BACKGROUND

A number of medical conditions may be treated in a minimally invasive manner with various kinds of catheters designed to reach treatment sites internal to a patient's body. Balloon catheters, for example, may be employed in angioplasty procedures to widen obstructed blood vessels and optionally deliver stents, or in procedures to treat atrial fibrillation, atrial flutter and ventricular tachycardia by forming therapeutic lesions in the soft tissue in the heart. In some procedures, expansion of the balloon at the treatment site may provide the desired therapy, such as expanding an obstructed blood vessel during an angioplasty procedure. In other procedures, an energy source within the balloon can deliver the desired therapy and, in these procedures, the balloon can serve to either position the energy source or communicate energy to or from the soft tissue to form the desired therapeutic lesions. For example, in procedures for treating atrial fibrillation, a balloon catheter can be used to position a radio frequency energy source in proximity to the tissue to be treated and, similarly, in cryoablation procedures for treating atrial fibrillation, a balloon catheter can be used to deliver cryotherapy or extract heat, through the surface of the balloon, from the soft tissue.

BRIEF SUMMARY

The present disclosure relates generally to medical devices and, more particularly, to dual balloon catheters. In one illustrative embodiment, a medical device may include a catheter shaft including a first tubular member and a second tubular member. The second tubular member may be disposed in a lumen of the first tubular member. The medical device may also include a first balloon and a second balloon. The first balloon may include a proximal waist coupled to an outer surface of the first tubular member. In some cases, the second balloon may be disposed within the first balloon and may include a proximal waist coupled to an inner surface of the first tubular member. In other cases, the second balloon may still be disposed within the first balloon, but may have the proximal waist coupled to a reduced outer diameter portion of the first tubular member.

In some cases, the first balloon may include a distal waist coupled to the second tubular member, and the second balloon may includes a distal waist coupled to the distal waist of the first balloon and/or the second tubular member.

In some cases, the catheter shaft may include one or more conduits in fluid communication with a space between the first balloon and the second balloon. The one or more conduits may be fluidly connected to the space between the first balloon and the second balloon via one or more openings in the outer tubular member or, in some instances, may extend into the space between the first balloon and the second balloon.

In another illustrative embodiment, a method of bonding a first balloon and a second balloon to a catheter shaft is disclosed. The method may include providing a catheter shaft including an outer tubular member and an inner tubular member, bonding a proximal waist of the first balloon to the outer tubular member of the catheter shaft, flaring a proximal waist of a second balloon, positioning the second balloon with the flared proximal waist over the first balloon and the catheter shaft, and bonding a distal waist of the second balloon to the inner tubular member and/or the distal waist of the first balloon. In some cases, the method may also include bonding a distal waist of the first balloon to the inner tubular member and bonding the flared proximal waist of the second balloon to the outer tubular member. In some instances, the proximal waist of the first balloon may be bonded to an inner surface of the outer tubular member. In other instances, such as when the outer tubular member includes a reduced outer diameter distal portion, the proximal waist of the second balloon may be bonded to the reduced outer diameter distal portion of the outer tubular member.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following detailed description of various illustrative embodiments of the disclosure in connection with the accompanying drawings, in which.

DETAILED DESCRIPTION

Figure 1:
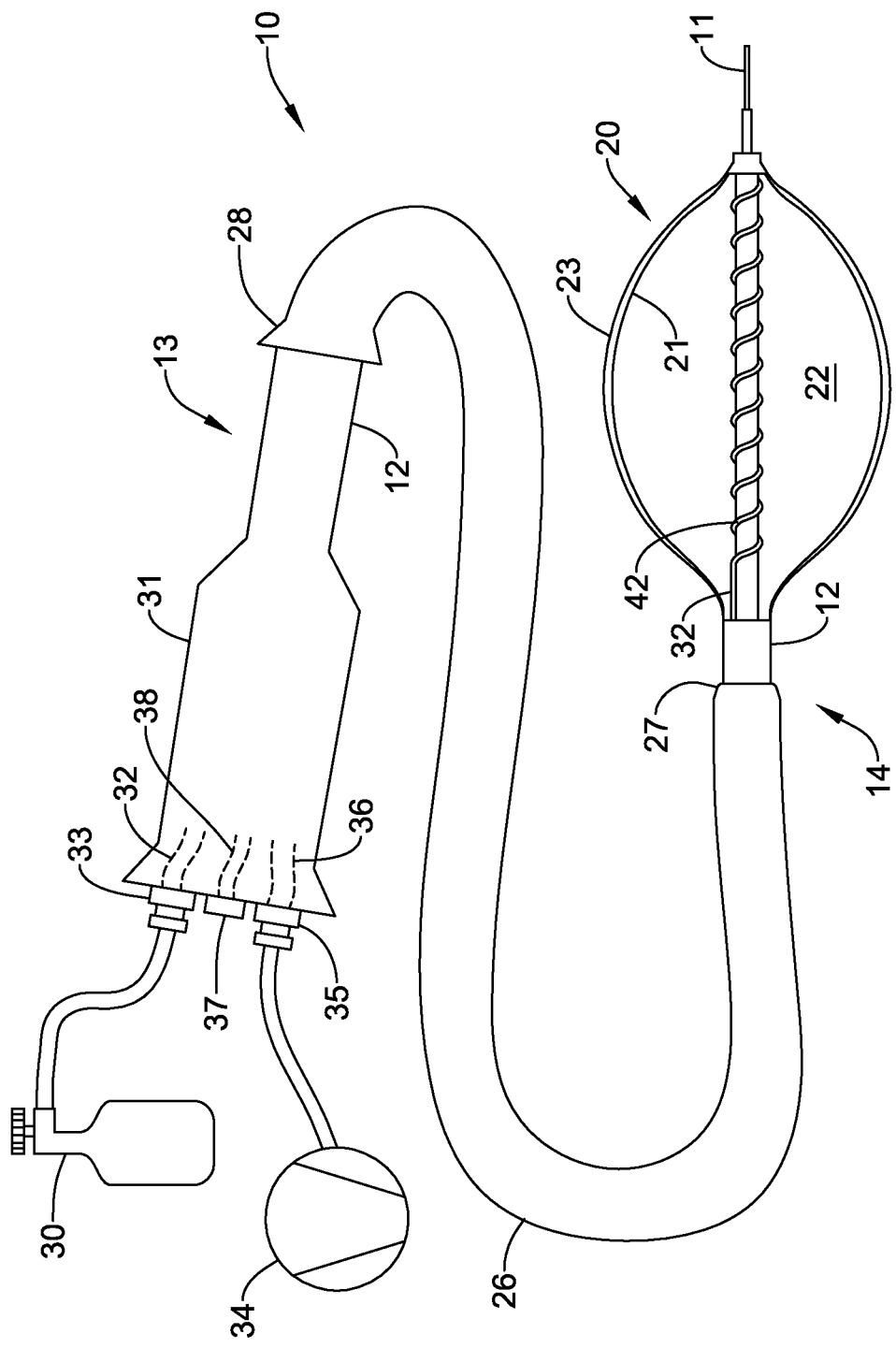
FIG. 1 is a schematic diagram of an illustrative embodiment of a balloon catheter.

The following description should be read with reference to the drawings wherein like reference numerals indicate like elements throughout the several views. The detailed description and drawings, which are not necessarily drawn to scale, show several embodiments which are meant to be illustrative and are not intended to limit the scope of the disclosure.

FIG. 1 is a schematic diagram of an illustrative embodiment of a balloon catheter 10. In the illustrative embodiment, the balloon catheter 10 may includes an elongate shaft 12 having a proximal section 13 and a distal section 14. An inflatable balloon assembly 20 may be disposed about at least a portion of the distal section 14 of the elongate shaft 12. As shown in FIG. 1, the balloon assembly 20 includes two balloons, an inner balloon 21 and an outer balloon 23. In the illustrative embodiment, the inner balloon 21 may define a chamber 22 for receiving a fluid (e.g. cryogenic fluid) and the outer balloon 23 may be disposed around the inner balloon 21. In some cases, the outer balloon 23 may function as a safety balloon to prevent the fluid from leaking out of the balloon assembly 20. That is, in the event that the inner balloon 21 ruptures or otherwise fails, the outer balloon 23 can prevent fluid (e.g., cryogenic fluid) from leaking out of the balloon assembly 20 and contacting body tissue internal to the patient.

In some embodiments, the inner balloon 21 and the outer balloon 23 may be configured to be inflated and deflated together or simultaneously, but this is not required. In other embodiments, separate inflation lumens (not shown) may be provided to independently inflate and deflate the inner balloon 21 and the outer balloon 23, as desired.

In the illustrative embodiment, inner balloon 21 and outer balloon 23 may be formed of any suitable material. For example, the inner balloon 21 and outer balloon 23 may be formed of any suitable non-compliant balloon materials. In other words, the inner balloon 21 and outer balloon 23 may be constructed to expand to a desired shape when pressurized without elastically deforming substantially beyond the desired shape. Example materials may include, for example, a polymer including but not limited to polyolefin copolymer, polyester, polyethylene teraphthalate, polyethylene, polyether-block-amide, polyamide (e.g. nylon), polyimide, latex, a urethane-family material, neoprene, etc. An example polyether-block-amide is available under the trade name PEBAX®. However, the foregoing materials are merely illustrative and it is contemplated that any suitable materials, either compliant or non-compliant, may be used. In some embodiments, inner balloon 21 and outer balloon 23 may be formed from the same or different material(s), as desired.

As illustrated in FIG. 1, the proximal section 13 of the balloon catheter 10 may include a port component 31 including a number of coupling members, such as coupling member 33 and 35, to facilitate coupling the balloon catheter 10 to external equipment. Example external equipment may include, for example, a source 30 of a cryogenic agent, a vacuum pump 34, and/or other desired external equipment. The coupling members 33 and 35 may be configured to be fluidly connected to and terminate at one or more lumens of the catheter shaft 12, such as a supply lumen 32 and an exhaust lumen 36. It is contemplated that the port component 31 may include additional coupling components fluidly connected to additional lumens, such as, for example, vacuum lumens, sensor lumens (e.g. pressure, temperature, etc.), and/or other lumens or combinations thereof. Further, the foregoing port component 31 is merely illustrative and is not meant to be limiting in any manner. It is contemplated that other suitable port components or port component configurations may be used, as desired.

In some embodiments, the balloon catheter 10 may be a cryotherapy balloon catheter and, in this embodiment, the balloon assembly 20 may be a cryo balloon configured to deliver cryotherapy to a treatment site internal to a patient. The cryo balloon assembly 20 may include at least one cooling region through which the cryotherapy can be delivered (or through which heat from adjacent body tissue can be extracted). In this example, the supply lumen 32 of the cryotherapy balloon catheter 10 may be configured to deliver fluid (e.g. cryogenic fluid) from external source 30 to the interior chamber 22 of the balloon assembly 20. As shown in FIG. 1, the supply lumen 32 may include a coiled portion 42 including one or more orifices (not shown) configured to release the cryogenic fluid in the interior chamber 22 of the balloon assembly 20. When so provided, at least some of the cryogenic fluid can undergo a liquid-to-gas phase change when released in the interior chamber 22 that cools the balloon assembly 20 by the Joule-Thomson effect. Gas resulting from the cryogenic fluid being released inside the chamber 22 can be exhausted through an exhaust lumen, such as lumen 36. The gas may be exhausted through the exhaust lumen 36 to the external vacuum pump 34.

As shown in FIG. 1, the coiled portion 42 of the supply lumen 32 may be helically wound around an inner tubular member (shown as 44 in FIG. 2) of the elongate shaft 12. In some cases, helically configuration of the coiled portion 42 of the supply lumen 32 may provide additional reinforcement to the inner tubular member. However, it is contemplated that the supply lumen 32 may be configured to include or not include a coiled portion, or have any other desired configuration. For example, supply lumen 32 may extend in a generally side-by-side or parallel arrangement with the inner tubular member, but this is just one example.

In some embodiments, the balloon catheter 10 may be an over-the-wire cryotherapy balloon catheter. In the illustrative example embodiment, the balloon catheter 10 may be advanced over a guidewire 11 to a desired location within a patient. To facilitate advancement of the balloon catheter 10 to the desired location, the catheter shaft 12 may define a guidewire lumen 38 for slidably receiving a guidewire 11. In some cases, the port component 31 may include a coupling for providing access to the guidewire lumen 38.

As shown in FIG. 1, the balloon catheter 10 can be disposed in a delivery sheath 26, however, it is contemplated that in other embodiments, the delivery sheath 26 may not be included. The illustrative delivery sheath 26 may be a hollow tube that can be initially placed inside a patient and subsequently used as a conduit for balloon catheter 10, as well as other medical devices. For example, when several catheters are used for a procedure, the delivery sheath 26 may help to protect the patient's internal body organs and/or body lumens through which the various medical devices are navigated. In addition, the delivery sheath 26 may also facilitate easier navigation of balloon catheter 10 and/or other medical devices by a physician or other technician to a treatment site.

In the illustrative embodiment, the delivery sheath 26 may be steerable, and it may be characterized by a specific diameter, length, distal feature, and/or other characteristics. For example, delivery sheaths may be available in varying diameters, such as, for example, 8.5 Fr (French), 10 Fr, 11 Fr.; varying lengths, such as, for example, 60 centimeters (cm), 65 cm, 71 cm, 78 cm, 90 cm.; and having distal ends that are biased in various shapes, such as, for example, in a 15 degree curve, a 55 degree curve, a short 120 degree curve, a long 120 degree curve. However, different delivery sheaths may be configured for different procedures, as desired. For example, a delivery sheath having one biased curvature may be particularly effective for guiding a cryo balloon to a patient's pulmonary veins to treat atrial fibrillation, while a delivery sheath having a different biased curvature may be particularly effective for another procedure, such as one in which a stent is delivered and positioned within a patient's vasculature.

As shown in FIG. 1, delivery sheath 26 may include a distal tip 27 that is slightly tapered to, for example, facilitate navigation of the distal sheath 26 through a patient's vasculature, or to facilitate crossing of tissue membranes of the patient (e.g. the septal wall during a procedure to treat atrial fibrillation). In some cases, the proximal end 28 of the delivery sheath 26 may be slightly flared or enlarged to more easily receive balloon catheter 10 and/or other medical devices.

Furthermore, the foregoing balloon catheter 10 and delivery sheath 26 are merely illustrative and are not meant to be limiting in any manner. It is contemplated that balloon catheter 10 may also include other components and/or structures that are typically found in balloon catheter or, more specifically, cryotherapy balloon catheters. For example, it is contemplated that balloon catheter 10 may include one or more sensors (e.g. temperature, pressure, etc) and sensor wires to monitor one or more parameters (e.g. temperature, pressure, etc) of the balloon catheter 10. Additionally, it is contemplated that balloon catheter 10 may include a biasing member, such as a spring, to bias the balloon assembly 20 to an extended configuration to facilitate delivery and/or withdrawal of the balloon catheter 10. An example biasing member is disclosed in U.S. application Ser. No. 13/312,725, published as U.S. 2012/0143130, which is hereby incorporated by reference.

FIGS. 2-5 are cross-sectional views of various balloon assemblies that may be employed by the balloon catheter 10 shown in FIG. 1. In some cases, the illustrative balloon assemblies may be configured to help reduce the outer profile (e.g. diameter) of the balloon catheter 10 and/or maintain a sufficient exhaust lumen space. The reduced outer profile may help facilitate withdrawal of the balloon catheter 10 into the guide catheter 26 after performing the cryoablation or other procedure. The sufficient exhaust space may help the balloon catheter 10 sufficiently exhaust the fluid (e.g. cryogenic fluid) during and/or after the cryoablation or other procedure. For mere simplicity, the supply lumen 32 is not shown in the illustrative balloon assemblies shown in FIG. 2-5, however, it is to be understood that the supply lumen 32 can be included.

Figure 2:
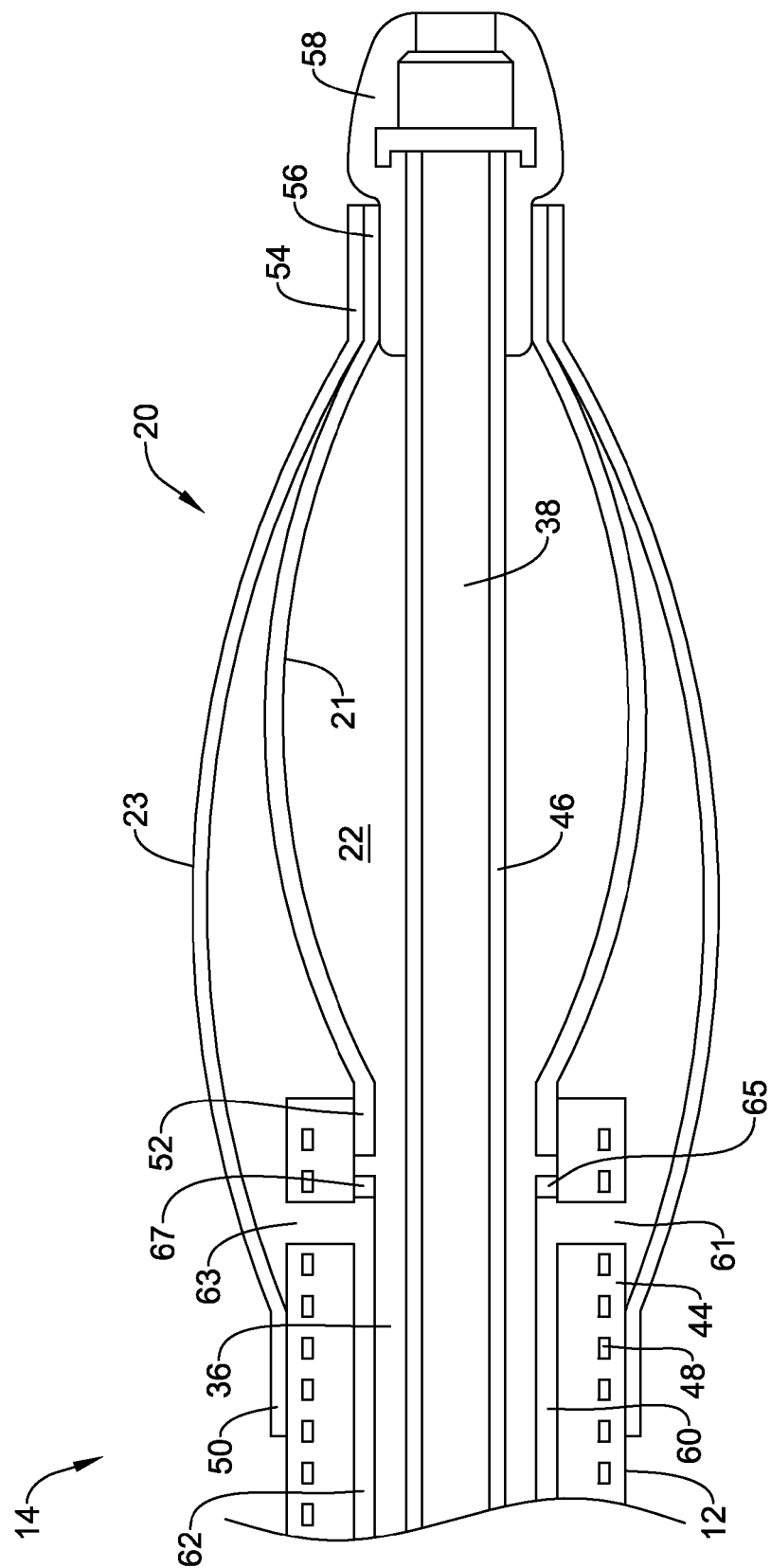
FIG. 2 is a cross-sectional view of an illustrative balloon assembly that may be employed by the balloon catheter shown in FIG. 1.

As shown in FIG. 2, the elongated shaft 12 may include an outer tubular member 44 and an inner tubular member 46 disposed within the outer tubular member 44. The inner tubular member 46 may define a guidewire lumen 38 and the annular-shaped lumen between the inner tubular member 46 and the outer tubular member 44 may define exhaust lumen 36. In some embodiments, the inner tubular member 46 and the outer tubular member 44 may be arranged such that the inner tubular member 46 extends distal of the outer tubular member 44.

In the illustrative embodiment, the outer tubular member 44 and inner tubular member 46 may be formed of suitable materials typically employed in catheter shafts. Example materials may include, for example, a polymer including but not limited to polyolefin copolymer, polyester, polyethylene teraphthalate, polyethylene, polyether-block-amide, polyamide (e.g. nylon), polyimide, latex, a urethane-family material, neoprene, etc. An example polyether-block-amide is available under the trade name PEBAX®. However, the foregoing materials are merely illustrative and it is contemplated that any suitable materials may be used, as desired. In some embodiments, inner tubular member 46 and the outer tubular member 44 may be formed from the same or different material(s), as desired.

In some embodiments, the outer tubular member 44 may be configured to include other components and/or structures. In one example, the outer tubular member 44 may include a reinforcement layer 48, such as a braid or coil, which may help to achieve desired pushability, torqueability, and/or flexibility characteristics. In another example, the outer tubular member 44 may include a distal extension including, for example, polyether-block-amide, bonded or otherwise connected to a distal end of the outer tubular member.

Furthermore, the foregoing elongate shaft 12 is merely illustrative and it is contemplated that other suitable elongate shafts may be used. For example, in some cases, the elongate shaft may be a multi-lumen shaft defining one or more lumens, such as vacuum lumens, exhaust lumens, supply lumens, pressure sensing lumens, temperature sensing lumens, and/or other lumens, as desired. An example multi-lumen shaft is disclosed in U.S. application Ser. No. 13/312,755, published as U.S. 2012/0150107, which is hereby incorporated by reference.

In the illustrative embodiment, the outer balloon 23 may include a proximal waist 50 bonded to an outer surface of outer tubular member 44 and the inner balloon 21 may include a proximal waist 52 bonded to an inner surface of outer tubular member 44. The example bonding configuration may provide a reduced outer profile (e.g. diameter) of the balloon catheter 10 relative to bonding both proximal waist 50 and 52 to the outer surface of the outer tubular member 44.

In some embodiments, a distal tip 58 may be disposed on the distal end of the inner tubular member 46. The distal tip 58 may include a lumen in fluid communication with guidewire lumen 38. In some cases, the distal waist 56 of the inner balloon 21 may be bonded to the distal tip 58 and the distal waist 54 of the outer balloon 23 may be bonded to the distal tip 58 and/or the distal waist 56 of inner balloon 21, but this is not required. In other cases, the distal waist 56 of the inner balloon 21 may be bonded directly to the inner tubular member 46 and the distal waist 54 of the outer balloon 23 may be bonded to the inner tubular member 46 and/or distal waist 56 of the inner balloon 21, as desired.

As shown in FIG. 2, the elongate shaft 12 may include one or more conduits, such as conduits 60 and 62, formed in or adjacent to the outer tubular member 44. In some cases, the conduits 60 and 62 may be in fluid communication with the space between balloons 21 and 23 via openings 61 and 63, respectively, formed in the outer tubular member 44. However, it is contemplated that other structures for fluidly connecting conduits 60 and 62 to the space between balloons 21 and 23 may be used, as desired. In some cases, one or more of conduits 60 and 62 may serve as vacuum lumens and may be used to apply a constant vacuum force between the balloons 21 and 23. Further, if balloon 21 ruptures, the constant vacuum force provided through conduits 60 and/or 62 may continue to evacuate any fluid (e.g. liquid or gas) that escapes the chamber 22 and enters the space between balloons 21 and 23. However, it is contemplated that conduits 60 and 62 may serve as other lumens, such as exhaust lumens, supply lumens, pressure sensing lumens, temperature sensing lumens, and/or other lumens, as desired. When utilized as pressure sensing lumens and/or temperature sensing lumens, conduits 60 and/or 62 may include one or more wires for pressure sensors and/or temperature sensors to monitor the temperature and/or pressure of various regions of the balloon catheter. For example, a pressure and/or temperature sensor may be configured to monitor the vacuum force between the balloons 21 and 23. If the vacuum force changes, the sensor may output a signal over a wire in the conduit 60 or 62 that may cause an alarm to be generated or corrective action to be taken, such as, for example, shutting off the cooling source 30.

In the illustrative embodiments, the conduits 60 and 62 may be formed from any suitable material. Example materials may include, for example, a polymer including but not limited to polyamide (e.g. nylon), polyimide, and polyether ether ketone (PEEK). However, the foregoing materials are merely illustrative and it is contemplated that any suitable materials may be used, as desired. In some cases, such as when conduits 60 and 62 are fluidly connected to the space between balloons 21 and 23 via openings 61 and 63, respectively, a distal end of conduits 60 and 62 may be filled or capped with an adhesive 65 and 67 or other suitable material to prevent fluid communication between conduits 60 and 62 and chamber 22 or exhaust lumen 36.

In some embodiments, the illustrative balloon assembly 20 may be assembled to the catheter shaft 12 using any suitable bonding process. For example, the proximal waist 52 of the inner balloon 21 may be bonded, fused, or otherwise connected to the inner surface of the outer tubular member 44. In some instances, the proximal waist 50 of the outer balloon 23 may then be flared and positioned over the distal section 14 of the elongate shaft 12, such as over the outer tubular member 44. Then, the proximal waist 50 of the outer balloon 23 can be bonded, fused, or otherwise connected to the outer surface of the outer tubular member 44.

Figure 3:
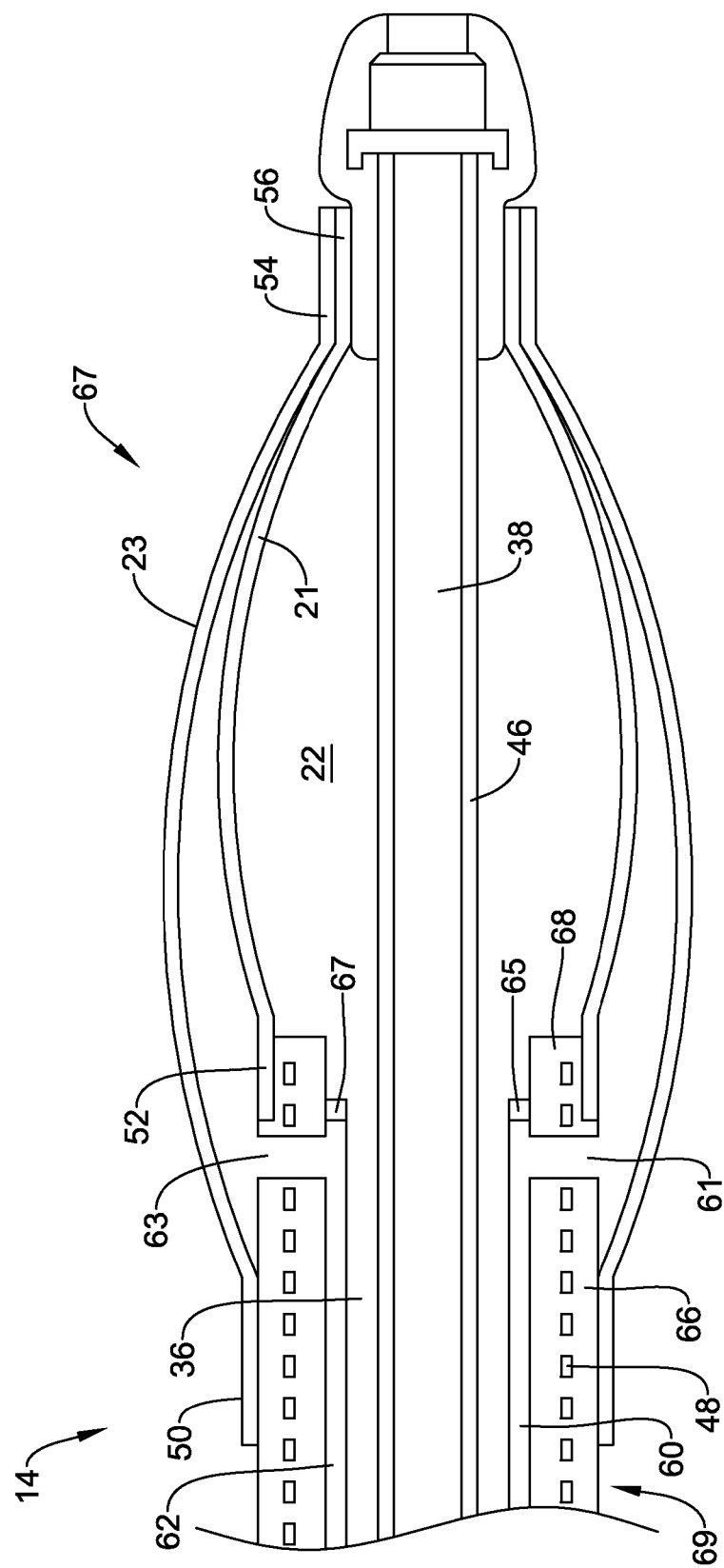
FIGS. 3-5 are cross-sectionals views of other balloon assemblies that may be employed by the balloon catheter shown in FIG. 1.

FIG. 3 is a cross-sectional view of another illustrative balloon assembly 67 that may be employed by the balloon catheter 10 shown in FIG. 1. In the illustrative embodiment, the elongate shaft 69 may be similar to elongate shaft 12, except outer tubular member 66 of elongate shaft 69 is configured to have a reduced outer diameter portion, shown as 68. In other words, portion 68 of outer tubular member 66 may have an outer diameter that is reduced relative to other portions (e.g. non-reduced portions) of outer tubular member 66, such as portions of outer tubular member 66 immediately proximal of portion 68. In some cases, the reduced outer diameter portion 68 may be formed by machining, grinding, or performing other manufacturing processes on the outer surface of the outer tubular member 66 to reduce the outer diameter. In other cases, a distal extension may be bonded to the distal end of the outer tubular member 66 to form the reduced diameter portion 68.

As shown in FIG. 3, the proximal waist 52 of the inner balloon 21 may be bonded to the outer surface of reduced diameter portion 68 of the outer tubular member 66. The proximal waist 50 of outer balloon 23 may then be bonded to the outer tubular member 66 (e.g. non-reduced diameter portion). However, it is contemplated that in other embodiments, the proximal waist 50 of the outer balloon 23 may be bonded to the reduced diameter portion 68 and/or the proximal waist 52 of inner balloon 21.

Figure 4:
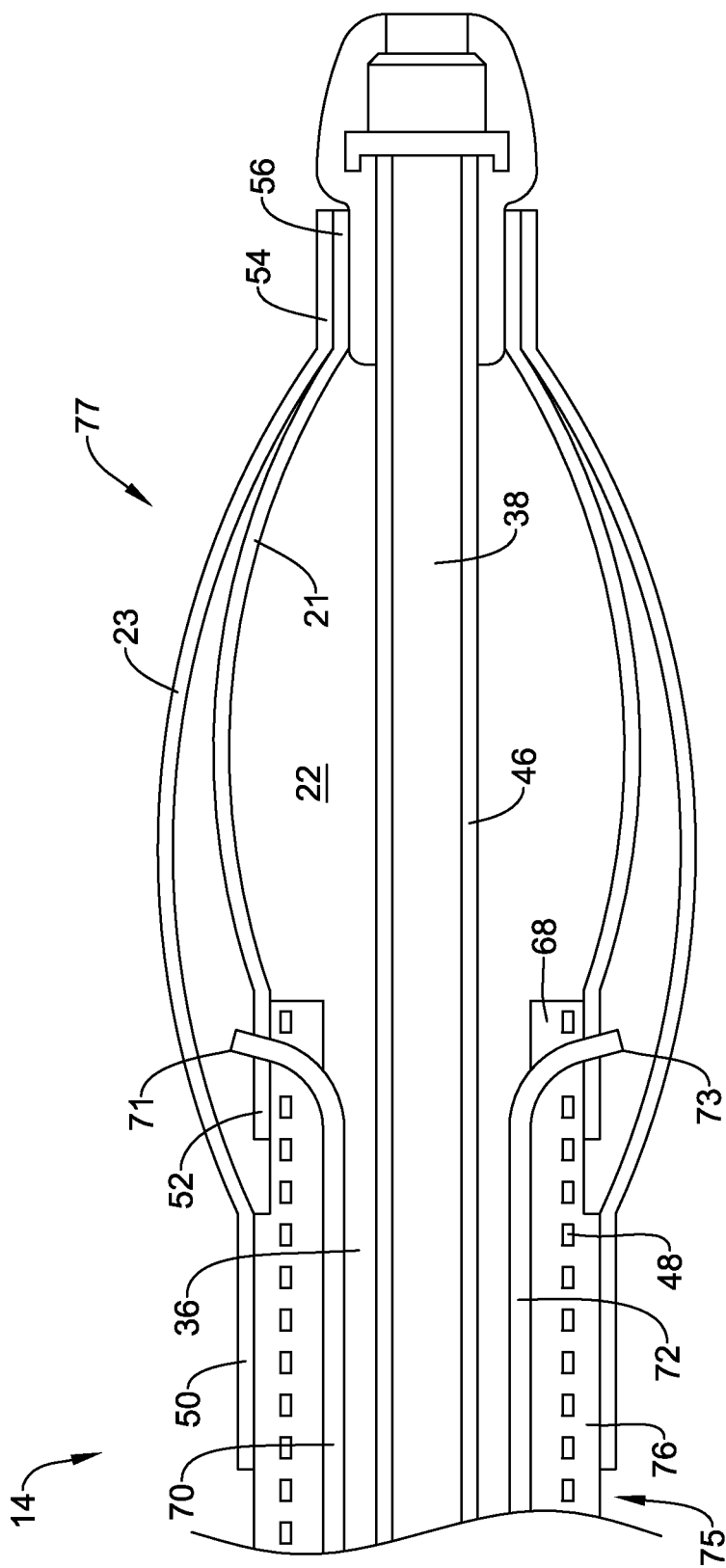

FIG. 4 is a cross-sectional view of another illustrative balloon assembly 77 that may be employed by the balloon catheter 10 shown in FIG. 1. In the illustrative embodiment, the elongate shaft 75 may be similar to elongate shaft 65 and may have conduits 70 and 72 similar to conduits 60 and 62. However, in the illustrative embodiment shown in FIG. 4, the distal end 71 of conduit 70 and the distal end 73 of conduit 72 may be configured and/or positioned to extend through the outer tubular member 76 and, in some instances, through the proximal waist 52 of inner balloon 21, into the space between balloons 21 and 23. In some instances, the conduits may extend about 1-2 millimeters (mm) into the space between balloons 21 and 23. However, other distances may be used, as desired.

In some embodiments, the proximal end 52 of the inner balloon 21 may be formed to include one or more openings to facilitate the insertion of the distal ends 71 and 73 of conduits 70 and 72 therethrough. In some cases, one or more openings may be formed prior to assembling the inner tubular member 21 over the elongate shaft 75, such as, for example, by poking or otherwise forming a hole through proximal waist 52.

As shown in FIG. 4, the proximal waist 52 of the inner balloon 21 may be bonded to the outer surface of reduced diameter portion 68 of the outer tubular member 75. The proximal waist 50 of the outer balloon 23 may be bonded to the outer tubular member 76 (e.g. non-reduced diameter portion). However, it is contemplated that proximal waist 50 of outer balloon 23 may be bonded to the reduced diameter portion 68 and/or the proximal waist 52 of inner balloon 21, as desired.

Figure 5:
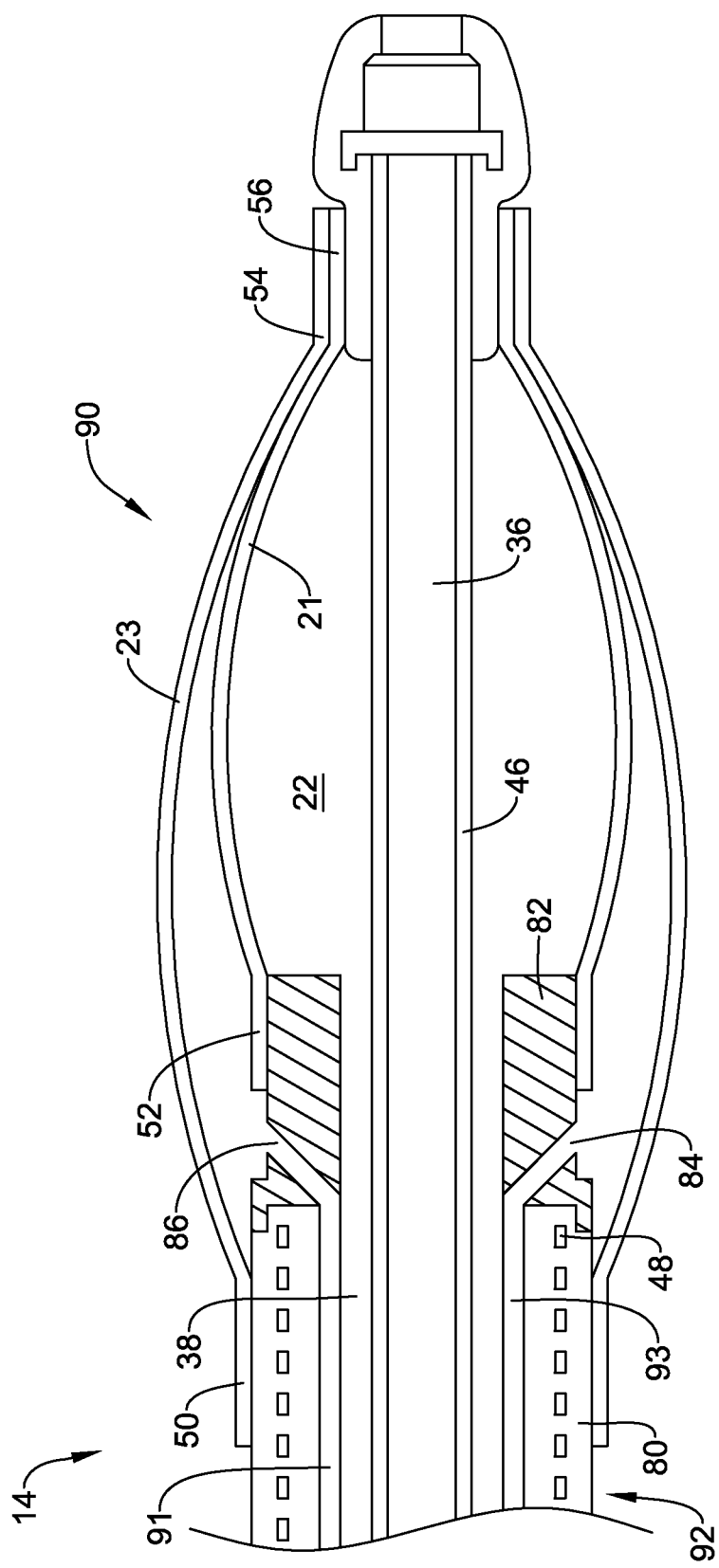

FIG. 5 is a cross-sectional view of another illustrative balloon assembly 90 that may be employed by the balloon catheter 10 shown in FIG. 1. In the illustrative embodiment, catheter shaft 92 may be similar to catheter shaft 69 and 75, except that catheter shaft 92 may include a distal extensions 82 attached or otherwise bonded to the distal end of outer tubular member 80. In this example, the distal extension 82 may form the reduced diameter portion of outer tubular member 80. The distal extension 82 may include any suitable material, such as for example, polyether-block-amide. However, other suitable materials may be used.

As shown in FIG. 5, the proximal waist 52 of the inner balloon 21 may be bonded to an outer surface of the distal extension 82 and the proximal waist 50 of the outer balloon 23 may be bonded to the outer surface of the outer tubular member 80. However, it is contemplated that proximal waist 50 of outer balloon 23 may be bonded to the distal extension 82 and/or the proximal waist 52 of inner balloon 21, as desired.

In the illustrative embodiment, conduits 91 and 93 may be similar to conduits 60 and 62, except that in the illustrative example, conduits 91 and 93 may be in fluid communication with the space between balloons 21 and 23 via openings 84 and 86. In some cases, openings 84 and 86 may be skived or otherwise formed in the distal extension 82.

While the foregoing has been described with reference to cryoablation catheters, this is not meant to be limiting in any manner. It is contemplated that other double balloon catheter may be used, as desired. Further, it is contemplated that the features of the various embodiments may be mixed and matched, as desired.

Having thus described the preferred embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The invention's scope is, of course, defined in the language in which the appended claims are expressed.

What is claimed is:

1. A medical device comprising:
   a catheter shaft including a first tubular member and a second tubular member, the first tubular member including a proximal region, a distal region, and a lumen extending therethrough, the second tubular member including a proximal region, a distal region, and a lumen extending therethrough, the second tubular member being at least partially disposed within the lumen of the first tubular member, wherein the distal region of the second tubular member is configured to extend distally of the distal region of the first tubular member;
   a first balloon including a proximal waist coupled to an inner surface of the first tubular member; and
   a second balloon disposed about the first balloon and including a proximal waist coupled to an outer surface of the first tubular member;
   wherein the first tubular member includes one or more conduits in fluid communication with a space between the first balloon and the second balloon, wherein the first tubular member includes one or more radially extending openings for fluidly connecting the one or more conduits with the space between the first balloon and the second balloon.

2. The medical device of claim 1, wherein the first balloon includes a distal waist coupled to the second tubular member, and wherein the second balloon includes a distal waist coupled to the distal waist of the first balloon and/or the second tubular member.

3. The medical device of claim 1, wherein the second tubular member lumen is a guidewire lumen.

4. The medical device of claim 1, wherein the catheter shaft defines an exhaust lumen between the inner surface of the first tubular member and an outer surface of the second tubular member.

5. The medical device of claim 1, wherein the catheter shaft defines a supply lumen, the supply lumen including a proximal end configured to be coupled to a fluid source for receiving a cooling fluid and a distal end in fluid communication with a chamber defined by the first balloon.

6. The medical device of claim 1, wherein a distal end of the one or more conduits is prevented from fluidly communicating with a chamber defined by the first balloon.

7. The medical device of claim 6, wherein the proximal waist of the first balloon is coupled to the first tubular member distal of the opening and the proximal waist of the second balloon is coupled to the first tubular member proximal of the opening.

8. The medical device of claim 1, wherein the proximal waist of the first balloon is coupled to the inner surface of the first tubular member at a point distal of the one or more openings.

9. A medical device comprising:
   a catheter shaft including a first tubular member and a second tubular member, the first tubular member including a proximal region, a distal region, and a lumen extending therethrough, the second tubular member including a proximal region, a distal region, and a lumen extending therethrough, the second tubular member being at least partially disposed within the lumen of the first tubular member, wherein the distal region of the second tubular member is configured to extend distally of the distal region of the first tubular member, wherein the distal region of the first tubular member includes a first outer diameter portion and a second reduced outer diameter portion;
   a first balloon including a proximal waist coupled to the reduced outer diameter portion of the first tubular member; and
   a second balloon disposed about the first balloon and including a proximal waist coupled to the first tubular member;
   wherein the catheter shaft includes one or more conduits in fluid communication with a space between the first balloon and the second balloon, wherein the first tubular member includes one or more openings fluidly connecting the one or more conduits with the space between the first and second balloons, the one or more openings extending through the first tubular member in the first outer diameter portion, such that the first outer diameter portion extends distal of the one or more openings.

10. The medical device of claim 9, wherein the first balloon includes a distal waist coupled to the second tubular member, and wherein the second balloon includes a distal waist coupled to the distal waist of the first balloon and/or the second tubular member.

11. The medical device of claim 9, wherein the second balloon is coupled to the first tubular member proximal of the reduced outer diameter portion.

12. The medical device of claim 9, wherein the reduced outer diameter portion of the first tubular member is formed by bonding a distal extension to the first tubular member.

13. The medical device of claim 9, wherein the second tubular member lumen is a guidewire lumen.

14. The medical device of claim 9, wherein the catheter shaft defines an exhaust lumen between the inner surface of the first tubular member and an outer surface of the second tubular member.

15. The medical device of claim 9, wherein the catheter shaft defines a supply lumen, the supply lumen including a proximal end configured to be coupled to a fluid source for receiving a cooling fluid and a distal end in fluid communication with a chamber defined by the first balloon.

16. The medical device of claim 9, wherein a distal end of the one or more conduits is prevented from fluidly communicating with a chamber defined by the first balloon.

17. A method of bonding a first balloon and a second balloon to a catheter shaft, the method comprising:
   providing a catheter shaft including an outer tubular member and an inner tubular member, the catheter shaft including one or more conduits;
   bonding a proximal waist of the first balloon to the outer tubular member of the catheter shaft;
   bonding a distal waist of the first balloon to the inner tubular member;
   flaring a proximal waist of a second balloon;
   positioning the second balloon with the flared proximal waist over the first balloon and the catheter shaft;
   bonding the flared proximal waist of the second balloon to the outer tubular member; and
   bonding a distal waist of the second balloon to the inner tubular member and/or the distal waist of the first balloon, wherein a space between the first balloon and the second balloon is in fluid communication with the one or more conduits, wherein the outer tubular member includes one or more openings fluidly connecting the one or more conduits with the space between the first and second balloons, the one or more openings extending radially through an outer wall of the outer tubular member such that the outer wall extends distal of the one or more openings.

18. The method of claim 17, wherein bonding the proximal waist of the first balloon to the outer tubular member of the catheter shaft included bonding the proximal waist of the first balloon to an inner surface of the outer tubular member.

19. The method of claim 17, wherein the outer tubular member includes a reduced outer diameter distal portion spaced apart distally from the one or more openings, and wherein bonding the flared proximal waist of the second balloon to the outer tubular member includes bonding the flared proximal waist of the second balloon to the reduced outer diameter distal portion of the outer tubular member.

* * * * *